US012653774B2

(12) United States Patent
Kalahasti et al.

(10) Patent No.: US 12,653,774 B2
(45) Date of Patent: Jun. 16, 2026

(54) TOPICAL COMPOSITIONS AND METHODS FOR USING SAME

(71) Applicant: MARY KAY INC., Addison, TX (US)

(72) Inventors: Geetha Kalahasti, Addison, TX (US); David Gan, Addison, TX (US)

(73) Assignee: MARY KAY INC., Addison, TX (US)

( * ) Notice: Subject to any disclaimer, the term of this patent is extended or adjusted under 35 U.S.C. 154(b) by 411 days.

(21) Appl. No.: 18/140,800

(22) Filed: Apr. 28, 2023

(65) Prior Publication Data

US 2023/0346688 A1 Nov. 2, 2023

Related U.S. Application Data

(60) Provisional application No. 63/336,622, filed on Apr. 29, 2022.

(51) Int. Cl.
| | |
|---|---|
| *A61K 36/00* | (2006.01) |
| *A61K 8/67* | (2006.01) |
| *A61K 8/73* | (2006.01) |
| *A61K 8/9728* | (2017.01) |
| *A61K 8/9789* | (2017.01) |
| *A61K 8/9794* | (2017.01) |
| *A61Q 19/08* | (2006.01) |

(52) U.S. Cl.
CPC ........... *A61K 8/9794* (2017.08); *A61K 8/671* (2013.01); *A61K 8/73* (2013.01); *A61K 8/9728* (2017.08); *A61K 8/9789* (2017.08); *A61Q 19/08* (2013.01)

(58) Field of Classification Search
CPC .................................................... A61Q 19/00
See application file for complete search history.

(56) References Cited

U.S. PATENT DOCUMENTS

| | | | |
|---|---|---|---|
| 9,549,957 | B2 | 1/2017 | John |
| 9,687,517 | B2 | 6/2017 | Collins et al. |
| 2016/0158144 | A1 | 6/2016 | Gan et al. |

| | | | | |
|---|---|---|---|---|
| 2017/0071214 | A1 | 3/2017 | Rehage | |
| 2020/0360734 | A1 | 11/2020 | Schmidt | |
| 2021/0244654 | A1* | 8/2021 | Carle | ..................... A61K 35/74 |
| 2021/0330581 | A1 | 10/2021 | Gan et al. | |

FOREIGN PATENT DOCUMENTS

| | | | | |
|---|---|---|---|---|
| CN | 111053716 A | * | 4/2020 | ............. A61P 17/18 |
| WO | WO 2013/149323 | | 10/2013 | |
| WO | WO 2020/052916 | | 3/2020 | |
| WO | WO 2021/165232 | | 8/2021 | |

OTHER PUBLICATIONS

International Search Report and Written Opinion issued in Corresponding PCT Application No. PCT/US2023/020350, dated Sep. 14, 2023.
Boudaka, Ammar, et al., "Role of Transient Receptor Potential Vanilloid 4 Channel in Skin Physiology and Pathology." *Sultan Qaboos University Medical Journal*, vol. 20, No. 2, 2020, pp. e138-e146.
Extended European Search Report issued in corresponding European Application No. 23797342.5, dated Mar. 4, 2026.
Kalahasti, G., et al., "LB726 The combination of 0.5% retinal with a naturally derived TRPV1 antagonist and anti-inflammatory botanical extract helps mitigate retinoid- induced irritation." *Journal of Investigative Dermatology*, vol. 141, No. 9, 2021, p. B6.
Kueper, Thomas, et al., "Inhibition of TRPV1 for the Treatment of Sensitive Skin." *Experimental Dermatology*, vol. 19, No. 11, 2010, pp. 980-986.

* cited by examiner

*Primary Examiner* — Qiuwen Mi
(74) *Attorney, Agent, or Firm* — NORTON ROSE FULBRIGHT US LLP

(57) ABSTRACT

The present invention relates generally to methods and compositions useful for soothing skin inflammation in a subject. In some embodiments, methods and compositions disclosed herein comprise topical administration of a cosmetic formulation, wherein the cosmetic formulation comprises at least one transient receptor potential channel vanilloid subtype 1 (TRPV-1) antagonist. In some embodiments, the composition and/or method comprises plankton extract (e.g., saccharide isomerate), *Phragmites communis* (common reed) extract, *Poria cocos* (China root) extract, and/or *Cucurbita pepo* (pumpkin) seed extract.

17 Claims, 5 Drawing Sheets

TOPICAL COMPOSITIONS AND METHODS FOR USING SAME

CROSS-REFERENCE TO RELATED APPLICATIONS

This application claims the benefit of priority to U.S. Provisional Patent Application Ser. No. 63/336,622, filed Apr. 29, 2022, hereby incorporated by reference in its entirety.

BACKGROUND

A. Field of the Invention

The present invention relates generally to the field of topical skin compositions. More particularly, it concerns the use of topical skin compositions to reduce skin irritation caused by agonist activation of transient receptor potential channel vanilloid subtype 1 (TRPV-1) (e.g., retinol activation).

B. Description of Related Art

Ageing, chronic exposure to adverse environmental factors, malnutrition, fatigue, etc., can change the visual appearance, physical properties or physiological functions of skin in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

Previous attempts to improve the visual appearance of skin with known skin active-ingredients have been shown to have various drawbacks such as skin irritation and prolonged recovery periods. Retinol (vitamin A) is one of the first FDA approved anti-aging treatments to be used in cosmetic formulations for the treatment of photodamaged skin and to delay the appearance of aging. Retinol binds to different receptors to modulate various cellular processes such as, but not limited to, keratinocyte differentiation, the blockage of transport of melanin to epidermal cells, inhibition of matrix metalloproteinases (MMPs) and/or stimulation of collagen fiber synthesis in fibroblasts. (M Zasada et al.; 2019). In addition, retinol can also increase the excitability of nociceptors (sensory neurons), and such an increase in excitability can lead to increased tissue sensitivity and/or irritation. Retinoid-elicited irritation is a primary cause for subject non-compliance with treatment regimens and/or discontinuation of retinol use before improved skin appearance is achieved. In addition, retinol overuse can also exacerbate skin dryness and/or burning sensations. Published literature describes up to 12% of subjects reporting adverse events (AEs) when using retinol. Skin inflammation can be a direct response to noxious chemosensory irritants. Certain cells, such as epidermal keratinocytes, melanocytes, and/or fibroblasts can also release cytokines in response to noxious stimuli, which in addition to other inflammatory effects, can also sensitize peripheral nociceptive fibers and produce neurogenic inflammation. Previous research has shown that retinol activates transient receptor potential channel vanilloid subtype 1 (TRPV-1), an irritant receptor for capsaicin (S Yin et al.; 2013).

Herein it is shown that a combination of one or more TRPV-1 antagonists (e.g., saccharide isomerate, pumpkin seed extract, common reed extract, and/or China root extract) can be used to suppress TRPV-1 mediated calcium flux and associated tissue irritation, such as anti-aging compound induced irritation (e.g., retinoid-induced irritation). Additionally, the inventors show that such TRPV-1 antagonism can optionally be combined with one or more pro-inflammatory cytokine inhibitors, and/or optionally combined with one or more anti-aging compound tolerance improvement protocols to further increase an individual's tolerance to treatment regimens comprising irritation inducing anti-aging compounds (e.g., hydroquinone, resorcinol, trichloroacetic acid, a carboxylic acid, a dicarboxylic acid, a beta-hydroxy acid, and/or an alpha-hydroxy acid).

SUMMARY

Methods and compositions of the present disclosure overcome deficiencies in the art by recognizing the importance of treatment regimen compliance and providing methods and compositions that improve the same. More specifically, the inventors have identified a set of compounds that act as TRPV-1 antagonists and inhibitors of the associated cellular calcium flux. In certain embodiments, disclosed TRPV-1 antagonists can be used alone, together, or in combination with other compounds to create compositions suitable for use in the field of cosmetology, nutraceuticals, and/or medicine, and methods of using the same.

In certain embodiments, disclosed herein are compositions suitable for combating the myriad signs of aging, while reducing adverse events associated with TRPV-1 activation by anti-aging compounds (e.g., a TRPV-1 agonist anti-aging compound), and/or while reducing adverse events associated with cytokine release induced by anti-aging compounds. In certain embodiments, an anti-aging compound may be but is not limited to hydroquinone, resorcinol, trichloroacetic acid, a carboxylic acid, a dicarboxylic acid, a beta-hydroxy acid, and/or an alpha-hydroxy acid. In certain embodiments, an alpha-hydroxy acid is citric acid, glycolic acid, lactic acid, malic acid, mandelic acid, and/or tartaric acid. In certain embodiments, a beta-hydroxy acid is salicylic acid, a derivative or metabolite of salicylic acid, beta hydroxybutanoic acid, tropic acid, and/or trethocanic acid. In certain embodiments, an agonist of TRPV-1 is retinol, a retinol precursor, a retinol derivative, and/or a retinol metabolite. In certain embodiments an agonist of TRPV-1 is resorcinol. In certain embodiments, an agonist of TRPV-1 is salicylic acid.

In certain embodiments, disclosed herein are compositions and/or methods suitable for reducing deep lines and wrinkles, evening uneven skin tone, lightening skin tone, increasing skin radiance, reducing photodamage, increasing elasticity of skin, increasing skin firmness, reducing sagging skin, reducing loss of facial volume, increasing skin barrier function, inhibiting anti-oxidant capacity in skin, increasing collagen expression in skin, increasing elastin expression in skin, increasing laminin expression in skin, inhibiting MMP-1, inhibiting MMP-3, inhibiting MMP-9, inhibiting pro-inflammatory cytokines, inhibiting elastase expression in skin, increasing fibronectin expression in skin, and/or reducing or mitigating erythema or redness in skin, skin dryness, peeling or flaking of skin, and/or skin irritation.

In some embodiments, topical skin compositions disclosed herein include any one of, any combination of, or all of plankton extract (e.g., saccharide isomerate), *Phragmites communis* (common reed) extract, *Poria cocos* (China root) extract, and *Cucurbita pepo* (pumpkin) seed extract. The amounts of the ingredients within the composition can vary (e.g., amounts can be as low as 0.000001% to as high as 80% w/w or any range therein). In certain embodiments, a composition comprising any one of, any combination of, or all of plankton extract (e.g., saccharide isomerate), *Phragmites communis* (common reed) extract, *Poria cocos* (China root) extract, and *Cucurbita pepo* (pumpkin) seed extract may be formulated as a composition designed to be applied prior to application of a composition comprising one or more anti-aging compounds (e.g., alpha hydroxy acids, retinol, etc.). In certain embodiments, a composition comprising any one of, any combination of, or all of plankton extract (e.g., saccharide isomerate), *Phragmites communis* (common reed) extract, *Poria cocos* (China root) extract, and *Cucurbita pepo* (pumpkin) seed extract further comprises one or more anti-aging compounds (e.g., alpha hydroxy acids, retinol, etc.). In certain embodiments, a composition comprising any one of, any combination of, or all of plankton extract (e.g., saccharide isomerate), *Phragmites communis* (common reed) extract, *Poria cocos* (China root) extract, and *Cucurbita pepo* (pumpkin) seed extract may be formulated as a composition designed to be applied after application of a composition comprising one or more anti-aging compounds (e.g., alpha hydroxy acids, retinol, etc.). In certain embodiments, compositions disclosed herein may further comprise any combination of one or more ingredients described herein. For example, in certain embodiments, a composition may comprise one or more additional ingredients selected from one or more active ingredients, conditioning agents, moisturizing agents, pH adjusters, structuring agents, inorganic salts, and/or preservatives. In certain embodiments, the disclosed compositions are utilized in any one or more methods described herein.

In certain embodiments, a composition disclosed herein does not comprise any one or more ingredients selected from one or more active ingredients, conditioning agents, moisturizing agents, pH adjusters, structuring agents, inorganic salts, and/or preservatives. In certain embodiments, a composition disclosed herein does not comprise *Argania spinosa* oil. In certain embodiments, a composition disclosed herein does not comprise tetrahexyldecyl ascorbate. In certain embodiments, a composition disclosed herein does not comprise *Acmella oleracea* extract. In certain embodiments, a composition disclosed herein does not comprise *Alpinia galanga* leaf extract. In certain embodiments, a composition disclosed herein does not comprise *Rosmarinus officinalis* (rosemary) leaf extract.

Methods of use for the compositions disclosed herein are also disclosed. In certain embodiments, compositions disclosed comprise, consist essentially of, or consist of any one of, any combination of, or all of plankton extract (saccharide isomerate), *Phragmites communis* (common reed) extract, *Poria cocos* (China root) extract, and/or *Cucurbita pepo* (pumpkin) seed extract. In some instances, the method comprises topically applying any one of the compositions disclosed herein to skin and/or the face and/or eye area in need thereof. In one aspect, any one of the compositions disclosed herein are topically applied and the composition is left on the application area, removed from the application area after a period of time, and/or removed directly after application.

In further embodiment, disclosed are compositions comprising, consisting essentially of, or consisting of any one of, any combination of, or all of plankton extract (saccharide isomerate), *Phragmites communis* (common reed) extract, *Poria cocos* (China root) extract, and/or *Cucurbita pepo* (pumpkin) seed extract. The composition can be included in a topical skin formulation, an injectable composition, an edible composition, or a nutraceutical. The composition can be in the form of an edible pill or gel cap or liquid or powder, or spray, or foam, or is aerosolized.

In particular aspects, the compositions of the present invention are formulated as a topical skin composition. The composition can have a dermatologically acceptable vehicle or carrier for the compounds, compositions and extracts. The composition can further include a moisturizing agent or a humectant, a surfactant, a silicone containing compounds, a UV agent, an oil, and/or other ingredients identified in this specification or those known in the art. The composition can be a lotion, cream, body butter, mask, scrub, wash, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, etc. The composition can be in powdered form (e.g., dried, lyophilized, particulate, etc.). The composition can be formulated for topical skin application at least 1, 2, 3, 4, 5, 6, 7, or more times a day during use. In some aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions of the present invention can also be modified to have a desired oxygen radical absorbance capacity (ORAC) value. In certain non-limiting aspects, the compositions of the present invention or the component or extracts thereof identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions, in non-limiting aspects, can have a pH of about 6 to about 9. In some aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include phenoxyethanol, methylparaben, propylparaben, or any mixture of thereof. In some embodiments, the composition is paraben-free.

Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also include any one of, any combination of, or all of the following additional ingredients: water, a conditioning agent, a chelating agent, a moisturizing agent, a pH adjuster, inorganic salts, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or more, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

The following enumerated aspects describe certain inventions disclosed herein.

Aspect 1 is a method of soothing skin inflammation in a subject comprising, topical administration of a cosmetic formulation, wherein the cosmetic formulation comprises at least one transient receptor potential channel vanilloid subtype 1 (TRPV-1) antagonist.

Aspect 2 is the method of aspect 1, wherein the at least one TRPV1 antagonist is saccharide isomerate, *Phragmites communis* extract and *Poria cocos* extract, and/or *Cucurbita pepo* (pumpkin) seed extract.

Aspect 3 is the method of aspect 1 or 2, wherein the cosmetic formulation comprises more than one TRPV-1 antagonist.

Aspect 4 is the method of any one of aspects 1-3, wherein the cosmetic formulation comprises at least 1% (w/v) saccharide isomerate.

Aspect 5 is the method of any one of aspects 1-4, wherein the cosmetic formulation comprises at least 5% (w/v) *Cucurbita pepo* (pumpkin) seed extract.

Aspect 6 is the method of any one of claims 1-5, wherein the cosmetic formulation comprises at least 1% (w/v) *Phragmites communis* extract and *Poria cocos* extract.

Aspect 7 is the method of any one of aspects 1-5, wherein the cosmetic formulation comprises at least 1% (w/v) *Phragmites communis* extract and/or *Poria cocos* extract.

Aspect 8 is the method of any one of aspects 1-7, wherein the topical administration results in inhibition of cellular calcium flux when compared to an appropriate relative control.

Aspect 9 is the method of any one of aspects 1-8, wherein the skin inflammation and/or irritation is or was caused by agonist activation of TRPV-1.

Aspect 10 is the method of aspect 9, wherein the agonist of TRPV-1 is an exfoliant.

Aspect 11 is the method of aspect 10, wherein the agonist of TRPV-1 is hydroquinone, resorcinol, trichloroacetic acid, a carboxylic acid, a dicarboxylic acid, a beta-hydroxy acid, and/or an alpha-hydroxy acid.

Aspect 12 is the method of aspect 11, wherein the alpha-hydroxy acid is citric acid, glycolic acid, lactic acid, malic acid, mandelic acid, and/or tartaric acid.

Aspect 13 is the method of aspect 11, wherein the beta-hydroxy acid is salicylic acid, a derivative or metabolite of salicylic acid, beta hydroxybutanoic acid, tropic acid, and/or trethocanic acid.

Aspect 14 is the method of aspect 9, wherein the agonist of TRPV-1 is retinol, a retinol precursor, a retinol derivative, and/or a retinol metabolite.

Aspect 15 is the method of aspect 14, wherein the formulation comprising retinol (vitamin A), a retinol precursor, a retinol derivative, or a retinol metabolite comprises at least 0.1 to 1% (w/v) of said ingredient.

Aspect 16 is the method of aspect 14 or 15, wherein the formulation comprising retinol and the cosmetic formulation comprising at least one TRPV-1 antagonist are the same composition.

Aspect 17 is the method of any one of aspects 1-16, further comprising administration of a formulation comprising at least one pro-inflammatory cytokine inhibitor.

Aspect 18 is the method of aspect 17, wherein the at least one pro-inflammatory cytokine inhibitor comprises *Rosmarinus officinalis* (rosemary) leaf extract.

Aspect 19 is the method of aspect 17 or 18, wherein the formulation comprising at least one pro-inflammatory cytokine inhibitor and the cosmetic formulation comprising at least one TRPV-1 antagonist are the same composition.

Aspect 20 is the method of aspect 19, wherein the composition comprises retinol.

Aspect 21 is the method of any one of aspects 17-20, wherein expression of interleukin-6 (IL-6), interleukin-8 (IL-8), and/or tumor necrosis factor alpha (TNFα) is inhibited when compared to an appropriate relative control.

Aspect 22 is the method of any one of aspects 1-21, wherein topical administration of the cosmetic formulation reduces erythema, edema, flaking, dryness, burning, stinging, and/or itching.

Aspect 23 is the method of any one of aspects 1-22, wherein when compared to an appropriate relative control, the administration of the cosmetic formulation results in improved skin pigmentation, reduction in fine lines and wrinkles, improved skin tone evenness, reduction of pho-todamage, and/or improved skin firmness.

Aspect 24 is the method of any one of aspects 1-23, wherein the cosmetic formulation is formulated for administration at least every other day for at least 4 weeks.

Aspect 25 is the method of aspect 24, wherein the cosmetic formulation is formulated for administration at least every other day for at least 8 weeks.

Aspect 26 is the method of any one of aspects 1-24, wherein the cosmetic formulation is formulated as a leave on product.

Aspect 27 is the method of any one of aspects 1-24, wherein the cosmetic formulation is formulated as a rinse off product.

Aspect 28 is a cosmetic formulation comprising, at least one TRPV1 antagonist selected from the group consisting of *Phragmites communis* extract and *Poria cocos* extract, Saccharide Isomerate, and *Cucurbita pepo* (pumpkin) seed extract, at least one cytokine inhibitor, and at least 0.1 to 1% (w/v) retinol.

Aspect 29 is the cosmetic formulation of aspect 28, wherein the composition comprises at least 1% (w/v) Saccharide Isomerate, at least 5% (w/v) *Cucurbita pepo* (pumpkin) seed extract, and/or at least 1% (w/v) *Phragmites communis* extract and *Poria cocos* extract.

Aspect 30 is the cosmetic formulation of aspect 28 or 29, wherein the composition comprises 0.5% (w/v) retinol.

It is contemplated that any embodiment discussed in this specification can be implemented with respect to any method or composition of the invention, and vice versa. Furthermore, compositions of the invention can be used to achieve methods of the invention.

In some embodiments, compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a serum, a gel, a wash, a body butter, a scrub, a foundation, a night cream, a lipstick, a cleanser, a toner, a sunscreen, a mask, an anti-aging product, a deodorant, an antiperspirant, a perfume, a cologne, etc.

"Topical application" means to apply or spread a composition onto the surface of lips or keratinous tissue. "Topical skin composition" includes compositions suitable for topical application on skin, lips, and/or keratinous tissue. Such compositions are typically dermatologically-acceptable in that they do not have undue toxicity, incompatibility, instability, allergic response, and the like, when applied to lips, skin, and/or keratinous tissue. Topical skin care compositions of the present invention can have a selected viscosity to avoid significant dripping or pooling after application to lips, skin, and/or keratinous tissue.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase, such as a measurable increase of a protein or molecule (e.g., matrix proteins such as fibronectin, laminin, collagen, or elastin or molecules such as hyaluronic acid) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is the ability to inhibit TRPV-1 mediated calcium flux, act as a TRPV-1 antagonist, and/or act as a soothing agent to minimize the activity of TRPV-1 agonists.

The phrase "and/or" means "and" or "or". To illustrate, A, B, and/or C includes: A alone, B alone, C alone, a combination of A and B, a combination of A and C, a combination of B and C, or a combination of A, B, and C.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

As noted above, in certain embodiments, the present invention provides a solution to the problems associated with current cosmetic products. In some embodiments, an effective amount plankton extract (saccharide isomerate), *Phragmites communis* (common reed) extract, *Poria cocos* (China root) extract, and/or *Cucurbita pepo* (pumpkin) seed extract, are utilized to inhibit TRPV-1 mediated calcium flux, and thus reduce adverse events, reduce unwanted side-effects, and/or increase subject treatment regimen compliance. Compositions comprising an effective amount plankton extract (saccharide isomerate), *Phragmites communis* (common reed) extract, *Poria cocos* (China root) extract, and/or *Cucurbita pepo* (pumpkin) seed extract, can be used to reduce lines and wrinkles, even skin tone, lighten skin tone, increase skin radiance, reduce photodamage, increase elasticity, increase skin barrier function, increase skin firmness, reduce sagging skin, as well as, or better than, certain other skin care compositions containing greater amounts of anti-aging compounds (e.g., alpha hydroxy acids, retinol, etc.).

In some embodiments, disclosed herein are compositions and methods for inhibition of cellular calcium flux, reduction of cell signaling molecule release, and/or subject compliance with cosmetic treatment regimens. In certain embodiments, compositions and methods disclosed herein reduce, inhibit, and/or substantively eliminate transient receptor potential cation channel subfamily V member 1 (TRPV-1) activity in response to noxious chemosensory stimuli (e.g., alpha hydroxy acids, retinol, etc.). In certain embodiments, such inhibition results in soothing of irritated tissues, reduction of tissue inflammation, reduction of tissue redness, and/or reduction of skin dryness. In certain embodiments, compositions and/or methods disclosed herein improve skin's visual appearance. In certain embodiments, compositions and/or methods disclosed herein improve a subject's compliance with clinician and/or manufacturer recommended treatment regimens. In certain embodiments, compositions and/or methods disclosed herein reduce discomfort, erythema, and/or skin dryness. In certain aspects, compositions disclosed herein & methods of using the same can include, but are not limited to, a combination of ingredients to exfoliate skin, reduce or eliminate irritation from exfoliation, reduce and/or eliminate the appearance of fine lines and/or wrinkles, renew skin, increase skin radiance, sooth skin, sooth tissues, reduce and/or eliminate inflammation, even skin tone, reduce the appearance of hyperpigmented skin, age spots, livers pots, and/or dark spots, and/or increase skin smoothness. In certain embodiments, compositions and/or methods described herein reduce unwanted side-effects, reduce adverse events, and/or increase subject compliance with treatment regimens.

Figure 1:
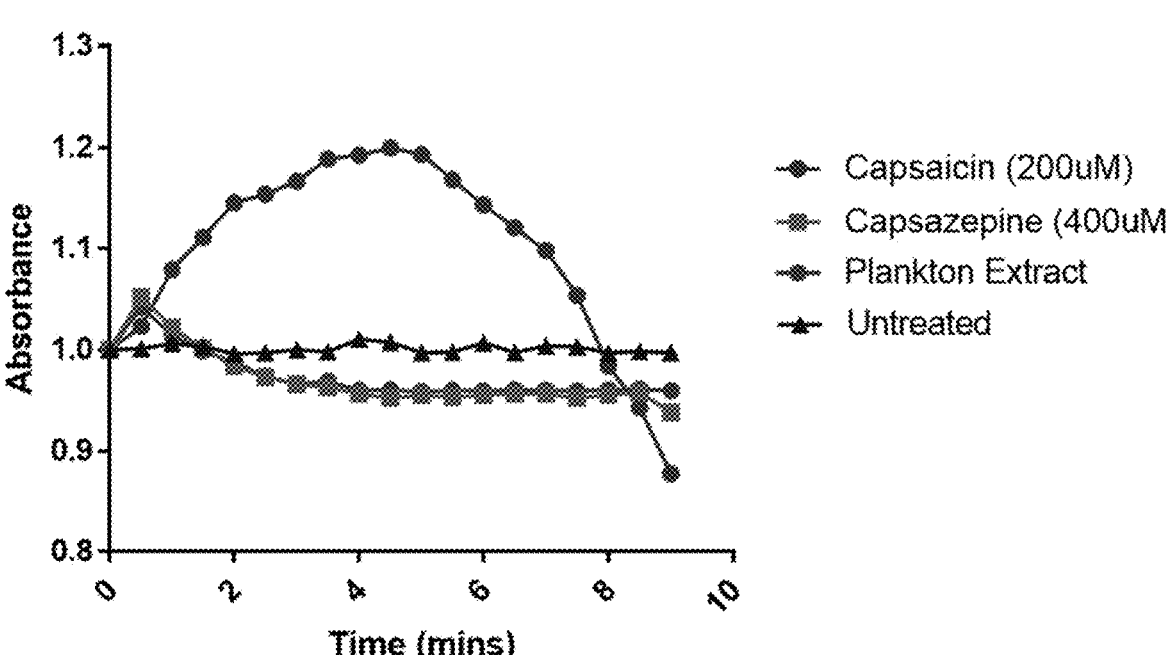
FIG. 1 depicts inhibition of cellular calcium flux by plankton extract (e.g., saccharide isomerate, also known as (aka) Benoitine). Briefly, $Ca^{2+}$ influx was used as a measure of TRPV-1 activity. PC 12 cells (ATCC CRL-1721) were pre-incubated for 4 hours at 37° C. with the respective noted compounds (e.g., plankton extract (test), or capsazepine (positive control)). Following pre-incubation, treatment media was removed and cells were incubated with 100 μl of 0.67 μM Fura-2-acetoxymethyl ester ((Fura-2AM), a high affinity, intracellular calcium indicator that is ratiometric and UV light—excitable) for 1 hour at 37° C. After incubation, cells were treated with 200 μM of capsaicin to induce TRPV-1 mediated $Ca^{2+}$ flux response and fluorescence readings were taken every 7 seconds for 10 minutes at 360/460 nm. Data was normalized to controls, plotted as shown, and area under the curve (AUC) values were determined (see Table 2). Cells incubated with plankton extract displayed a $Ca^{2+}$ flux profile similar to cells incubated with the positive control capsazepine, in that there was a brief increase of $Ca^{2+}$ flux which was quickly diminished in under 2 minutes.
Figure 2:
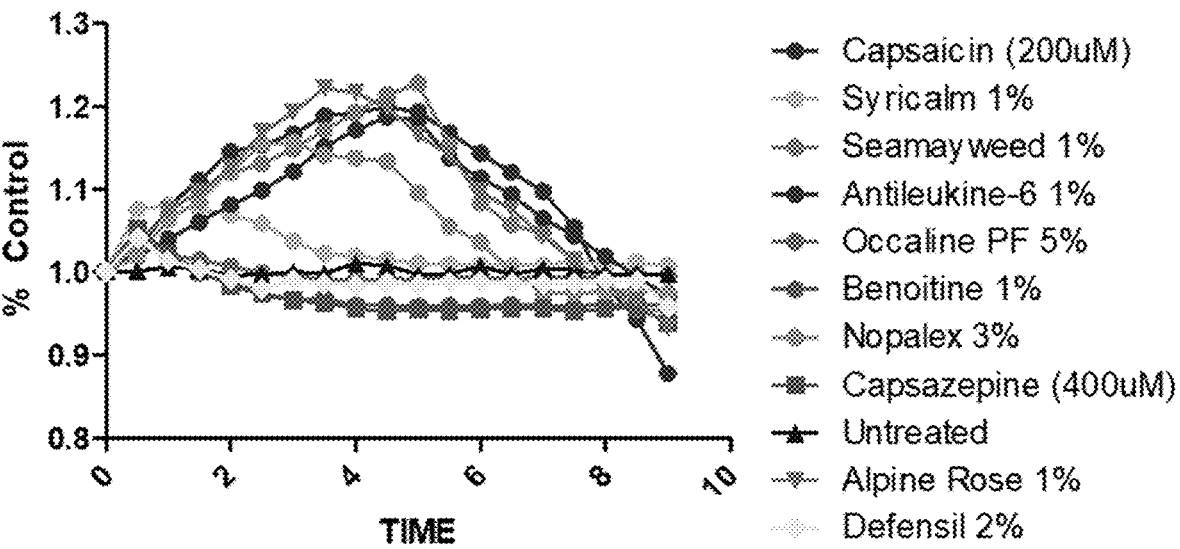
FIG. 2 depicts inhibition of cellular calcium flux by each of *Phragmites communis* (common reed) extract and *Poria cocos* (China root) extract (e.g., Syricalm™), *Cucurbita pepo* (pumpkin) seed extract (e.g., Ocâline™ PF), and plankton extract (e.g., saccharide isomerate, also known as Benoitine). Briefly, $Ca^{2+}$ influx was used as a measure of TRPV-1 activity. PC 12 cells (ATCC CRL-1721) were pre-incubated for 4 hours at 37° C. with the respective test compounds. Following pre-incubation, treatment media was removed and cells were incubated with 100 μl of 0.67 μM Fura-2AM for 1 hour at 37° C. After incubation, cells were treated with 200 μM of capsaicin to induce TRPV-1 mediated $Ca^{2+}$ flux response and fluorescence readings were taken every 7 seconds for 10 minutes at 360/460 nm. Data was normalized to controls, plotted as shown, and AUC values were determined (see Table 2). Cells pre-incubated individually with each of *Phragmites communis* (common reed) extract and *Poria cocos* (China root) extract (e.g., Syricalm™), *Cucurbita pepo* (pumpkin) seed extract (e.g., Ocâline™ PF), and plankton extract (e.g., saccharide isomerate, aka Benoitine) displayed a $Ca^{2+}$ flux profile similar to cells incubated with the positive control capsazepine, in that there was an increase of Ca2+ flux which was diminished in under 2 minutes, or 4 minutes respectively.
Figure 3:
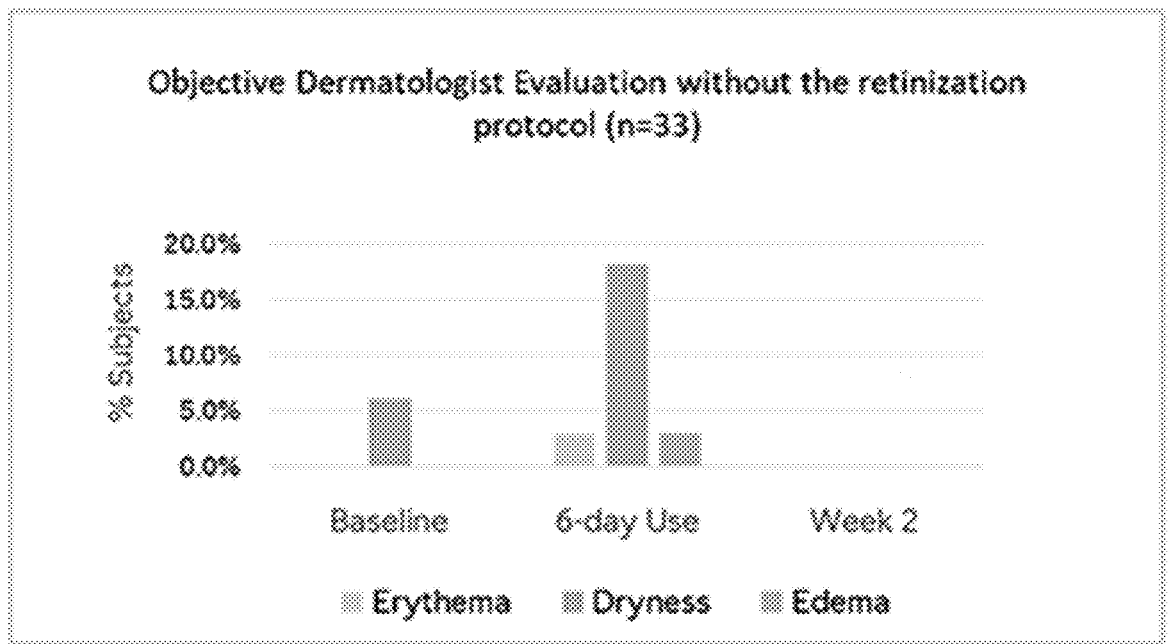
FIG. 3 depicts bar graphs noting results of clinical studies evaluating tolerability and efficacy of compositions comprising 0.5% retinol with (N=41 individuals) and without (N=33 individuals) implementation of a retinization protocol (e.g., gradual application of retinol over a period of time). The results show high tolerability and reduction in dermatologist-assessed erythema, edema, and dryness when using a retinization protocol. Panelist self-evaluations reported fewer moderate sensory discomfort scores and a reduction in erythema and dryness when using a retinization protocol.
Figure 3:
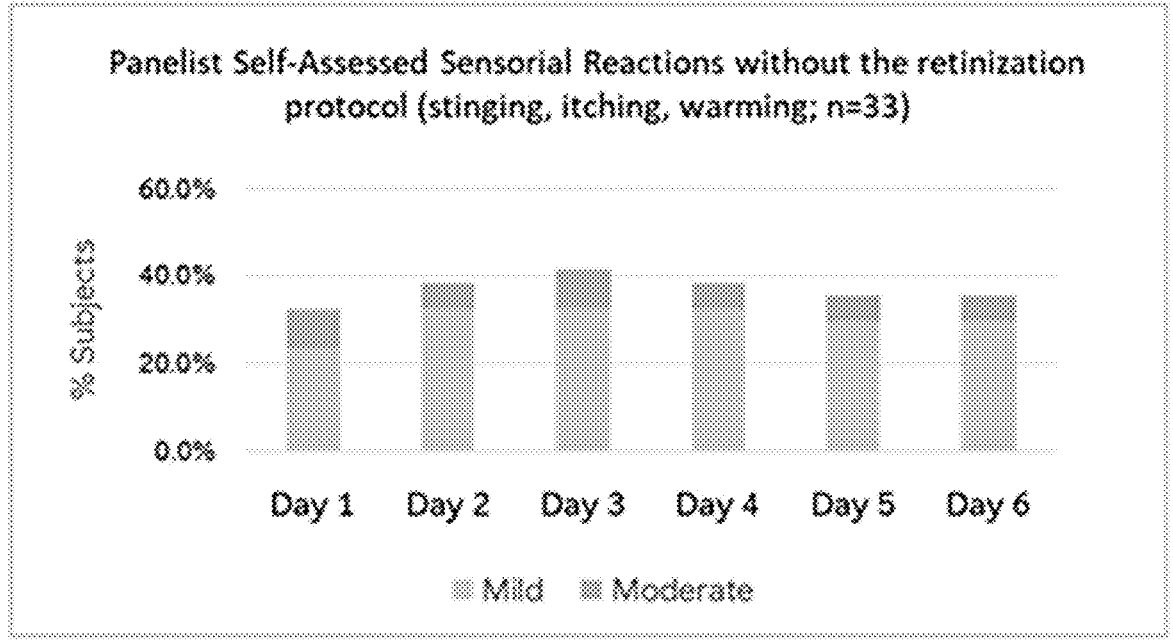
Figure 3:
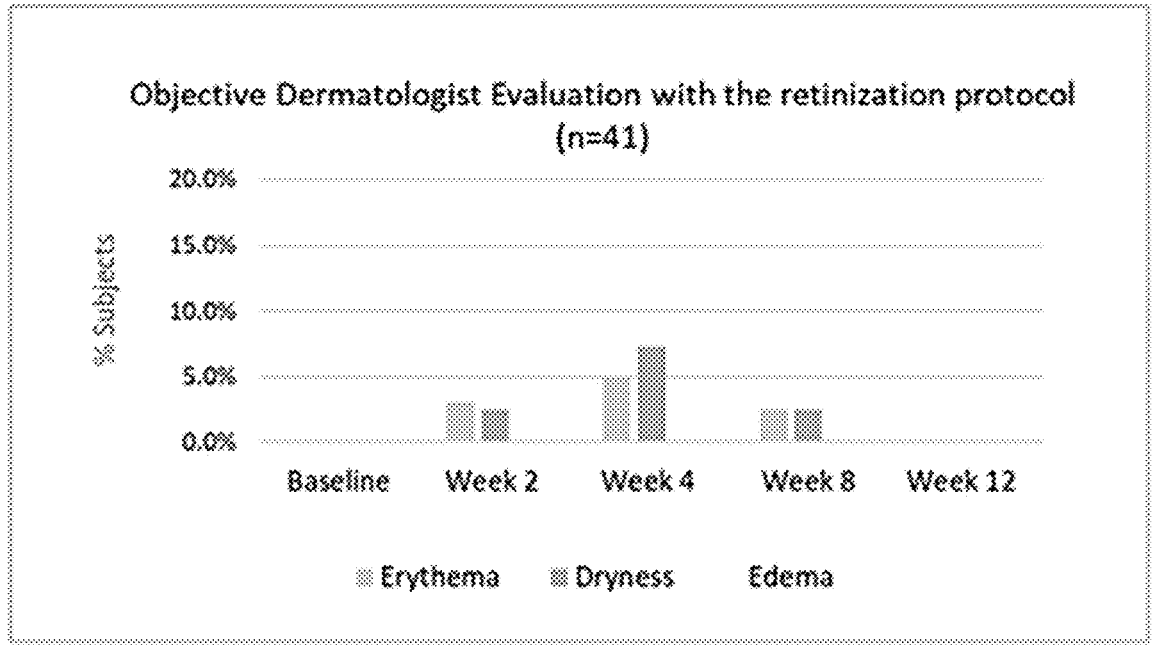
Figure 3:
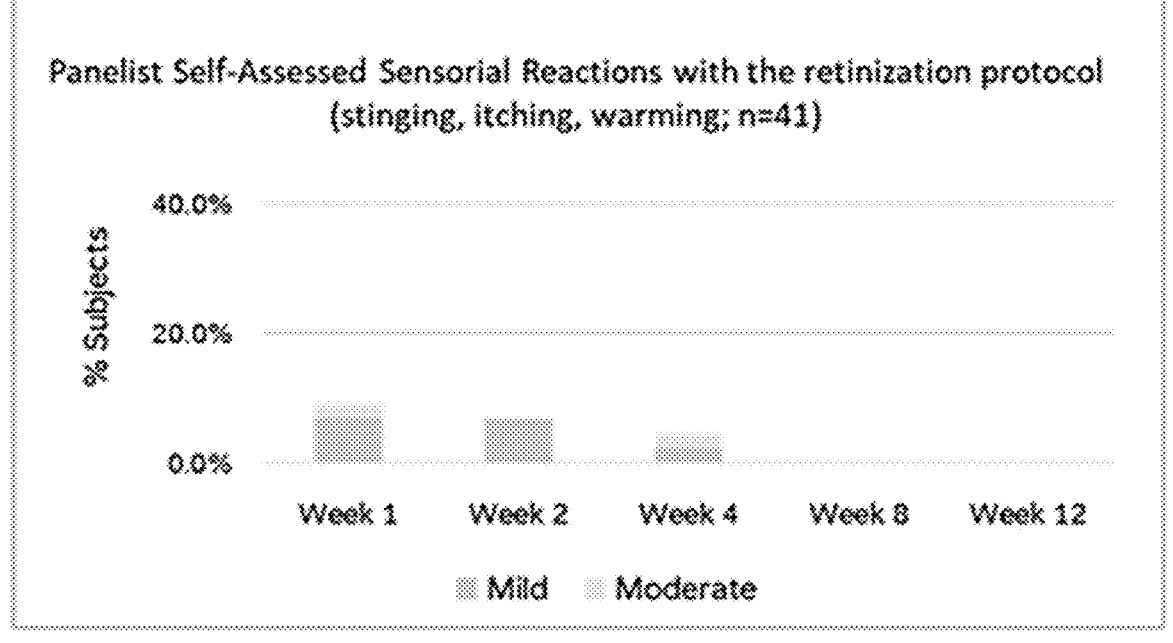
Figure 4:
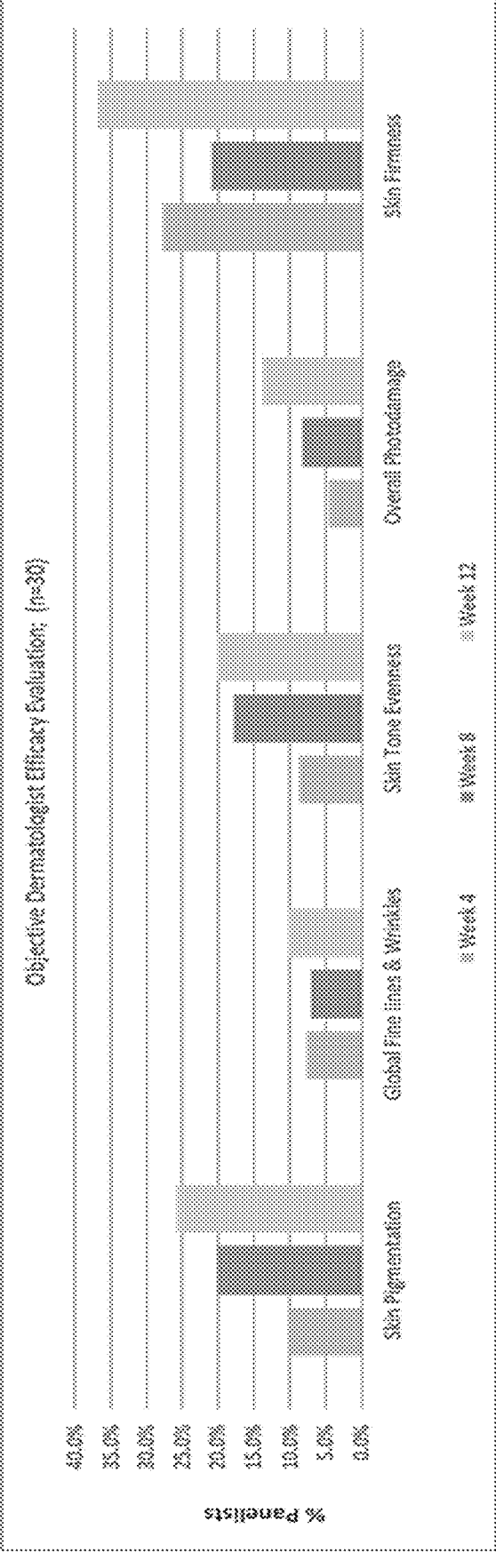
FIG. 4 depicts bar graphs noting results of a clinical study to evaluate skin hyperpigmentation, global fine lines and wrinkles, skin tone evenness, overall photodamage, and firmness as clinical measurements taken at 4 weeks, 8 weeks, and 12 weeks of use (N=30 individuals). Cosmetic formulations provided with implementation of a retinization protocol provided statistical improvements in each parameter (p<0.05) at both 4 and 8-weeks.

As shown in Table 2 and FIG. 2, each of plankton extract (saccharide isomerate), *Phragmites communis* (common reed) extract, *Poria cocos* (China root) extract, and/or *Cucurbita pepo* (pumpkin) seed extract, were shown to inhibit TRPV-1 mediated calcium influx. Furthermore, as shown in FIG. 3 and FIG. 4, administration of compositions comprising a TRPV-1 inhibitor improved subject and dermatologist described skin characteristics such as skin hyperpigmentation, global fine lines and wrinkles, skin tone evenness, overall photodamage, skin firmness, erythema, dryness, and/or edema.

In some embodiments, compositions comprising plankton extract (saccharide isomerate), *Phragmites communis* (common reed) extract, *Poria cocos* (China root) extract, and/or *Cucurbita pepo* (pumpkin) seed extract, can be designed to work as an emulsion (e.g., oil in water, water in oil), a gel, a serum, a gel emulsion, a gel serum, a lotion, a mask, a scrub, a wash, a cream, facial milk, sunscreen, cleansers, day cream, night cream, body butter, other skin treatment products, or any combination thereof.

Some compositions disclosed herein can be applied to the skin or hair and remain on the skin or hair for a period of time (e.g., at least 1, 2, 3, 4, 5, 10, 20, 30, or 60 minutes or more). After which, the composition, if needed, can be rinsed from the skin or peeled from the skin. Some compositions disclosed herein can be applied to the skin and immediately rinsed from the skin. Some compositions disclosed herein can be applied to the skin and absorbed at least in part by the skin.

Herein, the inventors show that addition of one or more TRPV-1 antagonists results in improved subject treatment regimen compliance and a reduction in dermatologist-assessed erythema, edema, and dryness in a cosmetic formulation containing an anti-aging compound (e.g., 0.5% retinol). Retinoids have been extensively used in the treatment of photoaging and many of them have shown significant clinical improvement. Although retinoids are a gold standard for the treatment of skin aging, reactions such as burning, scaling associated with their use is the primary reason for non-compliance or discontinuation. The retinization process described herein improved subject retinol tolerance by preventing irritation, enabling compliance throughout the study duration. Additionally, the Inventors show that less than 6% of subjects tested with a retinization regimen reported an adverse event during the study, indicating that a combination of TRPV-1 antagonists, nociceptors antagonists, and/or a gradual retinization process may be particularly beneficial components of successful compositions and/or methods related to combating the signs of aging, in particular by improving tolerability and mitigating anti-aging compound-elicited irritation. In some embodiments, provided herein are methods comprising, consisting essentially of, or consisting of a combination of TRPV-1 antagonists, nociceptors antagonists, and/or a gradual retinization process for combating the signs of aging, in particular by improving tolerability and mitigating anti-aging compound-elicited irritation (e.g., retinol elicited irritation, etc.).

In summary, the studies described herein demonstrate that TRPV-1 antagonists described herein can be used to mitigate the irritation effects associated with use of high doses of anti-aging compounds (e.g., alpha hydroxy acids, retinol, etc.). These and other non-limiting aspects of the present invention are described in the following sections.

A. Active Ingredients

Saccharide isomerate is an exopolysaccharide, which can be synthesized by a microorganism called *Vibrio alginolyticus*, belonging to the family of Thalasso plankton. In some instances, this ingredient is referred to as plankton extract. In some instances, this ingredient is commercially available from Barnet products, which supplies saccharide isomerate under the trade name Benoiderm™. In some instances, this ingredient is commercially available under the trade name Benoitine™, also supplied by Barnet products. It has been determined that an effective amount of saccharide isomerate can be used to inhibit TNFα. Herein it is shown that an effective amount of saccharide isomerate can be used to inhibit TRPV-1 mediated calcium flux.

*Phragmites communis*, is often referred to as "common reed", but also known as "perennial reed," "ditch reed," "giant reed," "reed grass," or "Arundo." It is a tall, robust, perennial grass commonly found in wetlands, marshes, riverbanks, and lakeshores. Traditionally, people have utilized the common reed to ameliorate symptoms associated with poor digestion, diabetes, leukemia, breast cancer, and insect bites. Common reed is known to contain vitamin A, vitamin C, and some B vitamins, but to our knowledge, an underlying causal ingredient or mechanism of action has yet to be publicly described. Herein it is shown that an effective amount of *Phragmites communis* extract can be used to inhibit TRPV-1 mediated calcium flux. In some instances, this ingredient is commercially available in combination with *Poria cocos* extract from Chemisches Laboratorium (CLR) under the trade "SyriCalm"™.

*Poria cocos* is a Polyporaceae saprophytic fungus that is commonly referred to as "China root," but is also known as "bracket fungus," "Fu-ling," "Fuling," "Hoelen," "Indian Bread," "Tuckahoe," "Sclerotium cocos," "Wolfiporia extensa," "Wolfiporia cocos," "Daedalea extensa," "Macrohyporia extensa," "Macrohyporia cocos," "Pachyma cocos," or "Medicine of Immortality." *Poria Cocos* grows in and/or on diverse species of Pine trees, and its sclerotium (vegetative resting spore) (known as "fuling" in Chinese) has been utilized as a traditional Chinese medicine for more than two thousand years. *Poria cocos* has a wide range of described biological activities including anti-tumor, immunomodulation, anti-inflammation, anti-oxidation, anti-ageing, anti-hepatitis, antidiabetic, and anti-haemorrhagic fever effects. *Poria cocos* polysaccharide (PCP) accounts for 84% by weight among all constituents in the dried sclerotium, and is thought to be the main bioactive component. Herein it is shown that an effective amount of *Poria cocos* extract can be used to inhibit TRPV-1 mediated calcium flux. In some instances, this ingredient is commercially available in combination with *Phragmites communis* extract from Chemisches Laboratorium (CLR) under the trade "SyriCalm"™.

*Cucurbita pepo* (pumpkin) seeds are derived from the subspecies *Cucurbita pepo* subsp. *Pepo*. The extract of pumpkin seeds has diverse bioactive compounds with potential nutraceutical and/or medical properties. The beneficial characteristics of pumpkin seed extract may be due to its strongly dichromatic viscous oil. Pumpkin has been utilized as a treatment option for hypertension and carcinogenic diseases, as an anti-diabetic, an anti-bacterial, an anti-oxidant, and/or as an anti-inflammatory. Herein it is shown that an effective amount of *Cucurbita pepo* seed extract can be used to inhibit TRPV-1 mediated calcium flux. In some instances, this *Cucurbita pepo* (pumpkin) seed extract is commercially available from Givaudan Active Beauty under the trade name "Ocâline"™.

The present invention is premised on a determination that any one of, any combination of, or all of plankton extract (saccharide isomerate), *Phragmites communis* (common reed) extract, *Poria cocos* (China root) extract, and/or *Cucurbita pepo* (pumpkin) seed extract can be used to inhibit TRPV-1 mediated calcium flux. In some embodiments, inhibition of TRPV-1 mediated calcium flux can sooth skin irritation, reduce skin inflammation, reduce skin redness, and/or reduce skin dryness.

The ingredients disclosed herein can be used in combination with various other cosmetically suitable ingredients, and/or can be used in different product forms to treat various skin conditions. By way of non-limiting examples, the combination of ingredients can be formulated in an emulsion (e.g., oil in water, water in oil), a gel, a serum, a gel emulsion, a gel serum, a lotion, a mask, a scrub, a wash, a cream, or a body butter.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the any ingredient within the compositions can vary. In non-limiting embodiments, for example, the compositions can comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition. In certain embodiments, compositions described herein do not comprise one or more of plankton extract (saccharide isomerate), *Phragmites communis* (common reed) extract, *Poria cocos* (China root) extract, and/or *Cucurbita pepo* (pumpkin) seed extract.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, scrubs, body butters, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis, Aloe barbadensis* extract, *Aloe barbadensis* gel, *Althea*

*officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (Santalum album) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (see U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds include silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers endblocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc.. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang-ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners include those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyl-taurate/VP copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid cross-linked with allyl ethers of sucrose or pentaerythritol (e.g., CARBOPOL™ 900 series from B. F. GOODRICH).

Non-limiting examples of crosslinked polyacrylate polymers include cationic and nonionic polymers. Examples are described in U.S. Pat. Nos. 5,100,660; 4,849,484; 4,835, 206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three units.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

k. Emollients

Useful emollients include the following: (a) silicone oils and modifications thereof such as linear and cyclic polydimethylsiloxanes; amino, alkyl, alkylaryl, and aryl silicone oils; (b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof; (d) hydrophobic plant extracts; (e) hydrocarbons such as liquid paraffins, vaseline, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and poly unsaturated fatty acids (PUFA); (g) higher alcohols such as lauryl, cetyl, stearyl, oleyl, behenyl, cholesterol and 2-hexydecanol alcohol; (h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; (i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; (j) lipids such as cholesterol, ceramides, sucrose esters and pseudo-ceramides as described in European Patent Specification No. 556,957; (k) vitamins, minerals, and skin nutrients such as vitamins A, E, and K; vitamin alkyl esters, including vitamin C alkyl esters; magnesium, calcium, and milk; (l) sunscreens such as octyl methoxyl cinnamate (Parsol MCX) and butyl methoxy benzoylmethane (Parsol 1789); (l) phospholipids; (m) polyhydric alcohols such as glycerine and propylene glycol; and polyols such as polyethylene glycols; (n) antiaging compounds such as alpha hydroxy acids, beta hydroxy acids; and (o) mixtures of any of the foregoing components, and the like.

l. Tackifiers

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar. (Non-polar meaning that the tackifier is substantially free of monomers having polar groups. Preferably, the polar groups are not present, however, if they are present, they are preferably present in an amount of up to about 5% by weight, preferably up to about 2% by weight, and more preferably up to about 0.5% by weight.).

m. Colorant

The compositions of the present invention may also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

n. Surfactant

Surfactants useful as the surfactant components in the compositions of the present invention include nonionic, anionic, cationic, and amphoteric (zwitterionic) surfactants and may be used in combination with each other.

o. pH Adjustors pH adjustors include inorganic and organic acids and bases and in particular aqueous ammonia, citric acid, phosphoric acid, acetic acid, sodium hydroxide, lactic acid, levulinic acid, glycolic acid, tartaric acid, malic acid, pyrrolidonecarboxylic acid (PCA), succinic acid, citric acid, glutamic acid, 2-amino-2-methyl-1-propanol (AMP), and triethanolamine (TEA).

p. Reducing Agents

Suitable reducing agents include, but are not limited to, thiourea, salts (such as sodium salts) of thiosulfate, sulfite, bisulfite, metabisulfite, borohydride, and hypophosphite, ascorbic acid and salts, esters, and derivatives thereof (e.g., ascorbyl palmitate and ascorbyl polypeptide), and tocopherols and salts, esters, and derivatives thereof (e.g., tocopherol acetate).

q. Fragrances

The compositions disclosed herein may optionally include a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora oil*, geranium maculatum oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus oxycedrus* tar, *Juniperus virginiana* oil, kiwi (*Actinidia chinensis*) water, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, and ylang (*Cananga odorata*) oil. Some non-limiting examples of synthetic hydrocarbon fragrances include caryophyllene, β-farnesene, limonene, α-pinene, and, β-pinene. Some non-limiting examples of synthetic alcohol fragrances include bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synethetic ester fragrances include benzyl acetate, 4-t-butylcyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin.

r. Foaming Agents

Foaming agents include, for example, sodium lauryl sulfate, sodium lauroyl sarcosine, sodium alkyl sulfosuccinates, sodium coconut oil fatty acid monoglycerol sulfonates, sodium α-olefin sulfonates, N-acylamino acid salts such as N-acyl glutamate, 2-alkyl-N-carboxymethyl-N-hydroxyethylimidazolinium betaine, maltitol fatty acid esters, sucrose fatty acid esters, polyglycerol fatty acid esters, fatty acid diethanolamides, polyoxyethylene sorbitan monostearate, polyoxyethylene hydrogenated castor oil and polyoxyethylene fatty acid esters. These foaming agents are usable either alone or in combination of two or more of them.

s. Tanning Agents

Suitable tanning agents include, without limitation, alpha-hydroxy aldehydes and ketones, glyceraldehyde and related alcohol aldehydes, various indoles, imidazoles and derivatives thereof, and various approved pigmentation agents. Other suitable tanning agents include, without limitation, methyl glyoxal, glycerol aldehyde, erythrulose, alloxan, 2,3-dihydroxysuccindialdehyde, 2,3 -dimethoxysuccindialdehyde, 2-amino-3-hydroxysuccindialdehyde and 2-benzylamino-3-hydroxysuccindialdehyde.

t. Astringents

Suitable astringents include, without limitation, aluminum citrate, aluminum lactate, extracts of birch, extracts of coffee, extracts of evening primrose, extracts of grape, extracts of henna, extracts of ivy, extracts of lemon, extracts of witch hazel, Ammonium and Potassium Alum, Aluminum Triphosphate, Aluminum Glycinate and Aluminum Phenolsulfate, Alcloxa, Aldioxa, Aluminum Stearate, Aluminum Sulfate and Aluminum Citrate, Sodium Aluminum Phosphate, Sodium Alum, Sodium Aluminum Chlorohydroxy Lactate, Calcium Lactate, Calcium Chloride, Calcium Sulfate Hydrate, Sodium Aluminum Lactate, Zinc Acetate, Zinc Chloride, Zinc Sulfate, Zinc Lactate, Zinc Zeolite, Zinc Phenolsulfonate, and combinations thereof. What is meant by an extract is either the whole fruit, bean, and/or plant or select constituents of such fruit, bean, and/or plant.

u. Antiseptics

Suitable antiseptics include, without limitation, methyl, ethyl, propyl, or butyl ester of p-oxybenzoic acid, phenoxyethanol, o-phenylphenol, dehydroacetic acid, or salts thereof, p-cresol, m-cresol, o-chlor-m-xylenol, peppermint oil, Echinacea, bloodroot, cayenne, tea tree oil, wild bergamont, chaparral, stinging metal, bay, myrrh, rhatany bark, toothache tree, calendula, chamomile, mupirocin, neomycin sulfate, bacitracin, polymyxin B, 1-ofloxacin, tetracyclines (chlortetracycline hydrochloride, oxytetracycline hydrochloride and tetrachcycline hydrochoride), clindamycin phsphate, gentamicin sulfate, benzalkonium chloride, benzethonium chloride, hexylresorcinol, methylbenzethonium chloride, phenol, quaternary ammonium compounds, triclocarbon, triclosan, and tea tree oil.

v. Deodorants and Antiperspirants

Suitable antiperspirants and deodorants include, without limitation, zinc salts such as zinc sulfate and zinc chloride, glycinates such as aluminum zirconium glycinate, aluminum chlorohydrate, aluminum zirconium tetrachlorohydrex, zinc carbonate, orthophenylphenol, and quaternary ammonium compounds such as dimethyl benzyl ammonium chloride and hexamethonium chloride.

w. Lighteners

Examples of skin lighteners include, without limitation, hydroquinone, kojic acid, licorice and/or its derivatives, ascorbic acid and/or its derivatives, arbutin, bearberry extract, Glycyrrhiza glabra and its derivatives, Chlorella vulgaris extract, perilla extract, coconut fruit extract, and/or other depigmenting agents.

x. Biocides

Examples of biocides include, without limitation, triclosan, 3,4,4'-trichlorocarbanilide (triclocarban); 3,4,4'-trifluoromethyl-4,4'-dichlorocarbanilide (cloflucarban); 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol(chloroxylenol); 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; miconazole; terconazole; butylparaben; ethylparaben; methylparaben; methylchloroisothiazoline; methylisothiazoline; a mixture of 1,3-bis(hydroxymethyl)5,5-dimethylhydantoin and 3-iodo-2-propynyl butyl carbamate; oxyquinoline; EDTA; tetrasodium EDTA; p-hydroxyl benzoic acid ester; alkyl pyridinum compounds; coco phosphatidyl PG-dimonium chloride; chlorhexidine gluconate; chlorhexidine digluconate; chlorhexidine acetate; chlorhexidine isethionate; chlorhexidine hydrochloride; benzalkonium chloride; benzethonium chloride; polyhexamethylene biguanide; and mixtures thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials Used

The active ingredients in Table 1 were used to obtain the in vitro and/or clinical data noted below and/or described in the associated drawings.

TABLE 1

| Ingredient |
| --- |
| Saccharide isomerate, supplied by Barnet Products under the tradename Benoitine ™. |
| *Phragmites communis* extract and *Poria cocos* extract, supplied by Chemisches Laboratorium (CLR) under the tradename SyriCalm ™. |
| *Cucurbita pepo* seed extract, supplied by Givaudan Active Beauty under the trade name Ocâline ™ PF. |

Example 2

In-Vitro Activities

It has been determined that any one of plankton extract (saccharide isomerate), *Phragmites communis* (common reed) extract, *Poria cocos* (China root) extract, and/or *Cucurbita pepo* (pumpkin) seed extract, can be used to inhibit TRPV-1 mediated calcium flux. A summary of results are found in Table 2 and the methods used to determine the properties of the ingredients are provided below.

Ingredient samples were analyzed for their ability to inhibit calcium flux production in PC 12 cells (ATCC CRL-1721). PC 12 cells were maintained and passaged according to the manufacturer's recommended guidelines. For experiments, $1 \times 10^5$ cells/well were plated in 96 well black flat bottom plates. Fura-2-Acetoxymethyl ester (Fura-2AM) calcium detection assay kit (Cayman Chemical #14591) was used to detect calcium in the cells post treatment. Capsaicin (Sigma #M202) was used to trigger a response, and capsazepine (Sigma #C191) was used as a positive control. In brief, $Ca^+$ influx was used as a measure of TRPV-1 activity. PC 12 cells (ATCC CRL-1721) were pre-incubated for 4 hours at 37° C. with the respective test compounds. Following pre-incubation, treatment media was removed and cells were incubated with 100 µl of 0.67 µM Fura-2AM for 1 hour at 37° C. After incubation, cells were treated with 200µM of capsaicin to induce TRPV-1 mediated $Ca^{2+}$ flux response and fluorescence readings were taken every 7 seconds for 10 minutes at 360/460 nm. Following the test period, buffer was removed and 100 µl diluted MTS reagent was added to each well. Cells were incubated for 15 to 30 minutes at 37° C. 5% $CO_2$, and plates were then read at 490 nm. Cell viability was assessed prior to analyzing for calcium flux.

Fluorescence test data was normalized to controls to generate area under the curve (AUC) values. For each control and test, fluorescence arbitrary units (AU) were normalized to controls for timepoints 0, and 0.5-9 minutes. The normalized data was plotted on an XY graph using GraphPad Prism software to generate a calcium flux curve, with time on the X axis, and normalized AU on the Y axis. The AUC was then calculated for the untreated control, and net AUC was determined for each test and control condition. Data for test conditions is expressed as percentage positive control (capsazepine 400 µM) (see Table 2 for results).

Cells pre-incubated individually with each of plankton extract (e.g., saccharide isomerate, aka Benoitine), *Phragmites communis* (common reed) extract and *Poria cocos* (China root) extract (e.g., Syricalm™), and *Cucurbita pepo* (pumpkin) seed extract (e.g., Ocâline™ PF) displayed a $Ca^{2+}$ flux profile similar to cells incubated with the positive control capsazepine, in that there was an increase of $Ca^{2+}$ flux which was diminished in under 2 minutes, or 4 minutes respectively.

TABLE 2

CAPSAICIN INDUCED TRPV-1 MEDIATED
CALCIUM FLUX ASSAY RESULTS

| Ingredient | Concen-tration | AUC | Delta compared to untreated | Percentage activity compared to positive control |
|---|---|---|---|---|
| Capsaicin (negative control) | 200 µM | 9.953 | 0.944 | −453.56 |
| Capsazepine (positive control) | 400 µM | 8.742 | −0.267 | NA (0) |
| Untreated (baseline control) | N/A | 9.009 | 0 | NA |
| Alpine Rose | 1% | 9.893 | 0.884 | −431.09 |
| Syricalm™ (common reed and China root extract) | 1% | 9.267 | 0.258 | −196.63 |

TABLE 2-continued

CAPSAICIN INDUCED TRPV-1 MEDIATED
CALCIUM FLUX ASSAY RESULTS

| Ingredient | Concen-tration | AUC | Delta compared to untreated | Percentage activity compared to positive control |
|---|---|---|---|---|
| Seamayweed | 1% | 9.843 | 0.834 | −412.36 |
| AntileukineTM-6 | 1% | 9.785 | 0.776 | −390.64 |
| Ocâline ™ PF (pumpkin seed extract) | 5% | 8.998 | −0.011 | −95.88 |
| Benoitine ™ (saccharide isomerate) | 1% | 8.968 | −0.041 | −84.644 |
| Nopalex | 3% | 9.947 | 0.538 | −301.5 |

Example 3

Clinical Studies

In a clinical study, it has been determined that subject treatment regimen compliance can be improved by including one or more TRPV-1 antagonists in the treatment regimen. A summary of results are found in FIG. 3 and FIG. 4, and the outline of the clinical study methods and results used to determine the properties of the ingredients are provided below.

The inventors conducted a series of clinical studies to evaluate the tolerability and efficacy of compositions comprising 0.5% retinol to develop a retinization protocol to improve tolerability in the general population. Study design included preliminary studies in which panelists used the retinol formulation every other night to establish a baseline sensory profile. Based on the results as shown in FIG. 3 and FIG. 4, and consultation with dermatologists, a gradual retinization protocol was developed to maximize tolerability and maintain efficacy. Study endpoints included dermatologist evaluation of erythema, edema, flaking, and dryness and panelist self-evaluation of burning stinging, itching. Additional clinical studies were conducted to evaluate skin hyperpigmentation, global fine lines and wrinkles, skin tone evenness, overall photodamage, firmness as clinical measurements. Generalized descriptions of the clinical studies performed related to the above evaluations can be found below in Example 4.

Example 4

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

B16 Pigmentation Assay: Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (MEDIATECH) at 37° C. in 10% $CO_2$ and then treated with any one of the active ingredients, combination of ingredients, or compositions having said combinations disclosed in the specification for 6 days. Following incubation, melanin secretion is measured by absorbance at 405 nm and cellular viability is quantified.

Collagen Stimulation Assay: Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured.

For generation of samples and controls, subconfluent normal human adult epidermal fibroblasts (Cascade Biologics) cultivated in standard DMEM growth medium with 10% fetal bovine serum (MEDIATECH) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from TAKARA (#MK101).

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers can be monitored in cultured human fibroblasts by staining of cultured human fibroblasts using immunofluorescent antibodies directed against elastin.

Laminin and Fibronectin Stimulation Assay: Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and intercellular adhesion of the epidermal calls to the DEJ. Laminin and fibronectin secretion can be monitored by quantifying laminin and fibronectin in cell supernatants of cultured human fibroblasts treated for 3 days with culture medium with or without 1.0% final concentration of the test ingredient(s). Following incubation, laminin and fibronectin content can be measured using immunofluorescent antibodies directed against laminin and antibodies directed against fibronectin in an enzyme linked immuno-sorbant assay (ELISA). Measurements are normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Tumor Necrosis Factor Alpha (TNF-α) Assay: The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EPILIFE™ standard growth medium (Cascade Biologics) at 37° C. in 5% $CO_2$, can be treated with phorbol 12-myristate 13-acetate (PMA, 10 ng/ml, SIGMA CHEMICAL, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Antioxidant (AO) Assay: An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®·+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, (β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS® oxidation is compared with that of Trolox, a water-soluble tocopherol analogue, and is quantified as molar Trolox equivalents. Anti-Oxidant capacity kit #709001 from CAYMAN CHEMICAL (Ann Arbor, Michigan USA) can be used as an in vitro bioassay to measure the total anti-oxidant capacity of each of any one of the active ingredients, combination of ingredients, or compositions having said combinations disclosed in the specification. The protocol can be followed according to manufacturer recommendations.

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Mushroom tyrosinase activity assay: In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (from SIGMA) can be incubated with its substrate L-Dopa (from FISHER) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test extract inhibition was compared with that of kojic acid (SIGMA).

Matrix Metalloproteinase 3 and 9 Enzyme Activity (MMP3; MMP9) Assay: An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoy]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M-1 cm-1 at pH 6.0 and above 7). The active ingredients, any one of the combination of ingredients, or compositions having said combinations disclosed in the specification can be assayed.

Matrix Metalloproteinase 1 Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The MOLECULAR PROBES ENZ/CHEK GELATINASE/COLLAGENASE/ASSAY kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The ENZ/CHEK GELATINASE/COLLAGENASE ASSAY kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, CAYMAN CHEMICAL) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, CAYMAN CHEMICAL) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay: ENZCHEK® Elastase Assay (Kit #E-12056) from MOLECULAR PROBES (Eugene, Oregon USA) can be used as an in vitro enzyme inhibition assay for measuring inhibition of elastase activity for each of the active ingredients, any one of the combination of ingredients, or compositions having said combinations disclosed in the specification. The ENZCHEK kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the ENZCHEK ELASTASE ASSAY KIT for screening for elastase inhibitors.

Production of Ceramides: Ceramides in cell or tissue samples can be labeled with a mouse monoclonal antibody anti-ceramide (ENZO LIFE SCIENCE, ref ALX-804-196 clone MID15B4) diluted to 1/50 for 2 hours at room temperature with an amplifier system biotin/streptavidin. Video microscope observation can be performed to view ceramides (pink stain).

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a MINOLTA chroma meter. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the MINOLTA chroma meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and are of the replicas covered by wrinkles or fine lines was determined.

Surface Contour of the Skin Assay with a Profilometer/Stylus Method: The surface contour of the skin can be measured by using the Profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200—MATTEK EPIL-IFE® growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin: Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% CO2 for 24 hours in EPILIFE™ growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by MILLIPORE (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in EPILIFE™ growth media with calcium from LIFE TECHNOLOGIES (M-EP-500-CA) supplemented with Keratinocyte Growth Supplement (HKGS) from LIFE TECHNOLOGIES (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Production of Hyaluronic Acid: Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells.

As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from SIGMA-ALDRICH (P1585) and platelet derived growth factor from SIGMA-ALDRICH (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

As another non-limiting example, human skin explants can be cultured in survival explants medium at 37° C. in a humidified atmosphere supplemented with 5% CO2. Treatment of the explants can be carried out by topical application of sample product (n=3) on days D0, D2, D3, D6, D8, and D9. The control explants (n=3) receive no treatment except renewal of survival explants medium. Half of the volume of the survival medium can be renewed at days D3, D6, and D8. At D9, three explants of each condition can be taken and cut in half. A half explant is fixed in buffered formalin and the other is frozen at −80° C.

After 48 hours of fixation in ordinary Bouin and 24 hours in formalin, the samples can be dried and soaked in paraffin using an automatic tissue processor Leica TP 1020. Sections of 5 microns can be performed with a microtome (Minot type LEICA RM2125) and mounted on SUPERFROST™ histological slides. Microscopic observations can be performed by optical microscopy, using a LEICA ORTHO-PLAN or LEICA DM LB microscope. Images can be taken with an OLYMPUS DP72 camera and CELLA^D software. General morphology can be examined on paraffin sections stained with Masson's trichrome Goldner variant. The staining of hyaluronic acid can be performed with an anti-hyaluronic acid biotinylated protein (HABP) (SEIK-AGAKU ref 400763-1A) diluted to 1/100 for 1 hour at room temperature, with an amplifier system biotin/streptavidin (VECTOR, VECTASTAIN PK-7200).

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from SIGMA-ALDRICH protocol #EC 3.2.1.35. Briefly, hyaluronidase type 1-S from SIGMA-ALDRICH (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-α is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine array: Human epidermal keratinocytes are cultured to 70-80% confluency. The media in the plate is aspirated and 0.025% trypsin/EDTA is added. When the cells became rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells became approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 μl of 100X stock) and 0.1% (10 μl of 100X stock) test compositions are diluted into a final volume of 1 ml EPILIFE™ Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (WHATMAN BIOSCIENCES), and the slides are placed into a FASTFrame (4 slides per frame) for processing. Arrays are blocked for 15 min. at room temperature using 70 ml S&S PROTEIN ARRAY BLOCKING BUFFER (WHATMAN SCHLEICHER AND SCHEULL). Blocking buffer is removed and 70 ml of each supernatant sample is added to each array. Arrays are incubated for 3 hours at room temperature with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temperature with gentle agitation. Arrays are washed 3 times with TBS-T. Arrays are incubated with 70 ml of a solution containing streptavidin-Cy5 conjugate for 1 hour at room temperature with gentle agitation. Arrays are washed 3 times with TBS-T, quickly rinsed in de-ionized water, and dried.

Slides can be imaged in a PERKIN-ELMER SCANAR-RAY 4000 confocal fluorescent imaging system. Array images can be saved and analyzed using IMAGING RESEARCH ARRAYVISION software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 μg/ml bovine brain extract, 1 μg/ml hydrocortisone, and 1 μg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses in 50 μl volume is applied into the formed capillary tubule cultures as treatment conditions. The no-treatment controls can be added with vehicle of test agents. SUTENT®, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of soothing skin inflammation in a subject comprising, topical administration of a cosmetic formulation, wherein the cosmetic formulation comprises at least one transient receptor potential channel vanilloid subtype 1 (TRPV-1) antagonist, wherein the at least one TRPV1 antagonist is a combination of saccharide isomerate, *Phragmites communis* extract and *Poria cocos* extract, and *Cucurbita pepo* seed extract.

2. The method of claim 1, wherein the cosmetic formulation comprises at least 1% (w/v) saccharide isomerate, at least 5% (w/v) *Cucurbita pepo* seed extract, and at least 1% (w/v) *Phragmites communis* extract and *Poria cocos* extract.

3. The method of claim 1, wherein the topical administration results in inhibition of cellular calcium flux when compared to an appropriate relative control.

4. The method of claim 1, wherein the skin inflammation is or was caused by agonist activation of TRPV-1.

5. The method of claim 4, wherein the agonist of TRPV-1 is hydroquinone, resorcinol, trichloroacetic acid, a carboxylic acid, a dicarboxylic acid, a beta-hydroxy acid, and/or an alpha-hydroxy acid.

6. The method of claim 5, wherein the alpha-hydroxy acid is citric acid, glycolic acid, lactic acid, malic acid, mandelic acid, and/or tartaric acid; and/or wherein the beta-hydroxy acid is salicylic acid, a derivative or metabolite of salicylic acid, beta hydroxybutanoic acid, tropic acid, and/or trethocanic acid.

7. The method of claim 6, wherein the agonist of TRPV-1 is retinol, a retinol precursor, a retinol derivative, and/or a retinol metabolite.

8. The method of claim 7, wherein the formulation comprising retinol, a retinol precursor, a retinol derivative, or a retinol metabolite comprises at least about 0.1 to 1% (w/v) of said ingredient.

9. The method of claim 7, wherein the formulation comprising retinol and the cosmetic formulation comprising at least one TRPV-1 antagonist are the same composition.

10. The method of claim 1, further comprising administration of a formulation comprising at least one pro-inflammatory cytokine inhibitor.

11. The method of claim 10, wherein the at least one pro-inflammatory cytokine inhibitor comprises *Rosmarinus officinalis* leaf extract.

12. The method of claim 10, wherein the formulation comprising at least one pro-inflammatory cytokine inhibitor and the cosmetic formulation comprising at least one TRPV-1 antagonist are the same composition, and optionally the composition further comprises retinol.

13. The method of claim 12, wherein expression of interleukin-6 (IL-6), interleukin-8 (IL-8), and/or tumor necrosis factor alpha (TNFα) is inhibited when compared to an appropriate relative control.

14. The method of claim 1, wherein the topical administration of the cosmetic formulation reduces erythema, edema, flaking, dryness, burning, stinging, and/or itching.

15. The method of claim 1, wherein when compared to an appropriate relative control, the topical administration of the cosmetic formulation results in improved skin pigmentation, reduction in fine lines and wrinkles, improved skin tone evenness, reduction of photodamage, and/or improved skin firmness.

16. The method of claim 1, wherein the cosmetic formulation is formulated for administration at least every other day for at least 4 weeks and/or for at least 8 weeks.

17. The method of claim 16, wherein the cosmetic formulation is formulated as a leave on product or as a rinse off product.

\* \* \* \* \*